United States Patent
Carter et al.

(10) Patent No.: US 12,424,305 B2
(45) Date of Patent: Sep. 23, 2025

(54) CLOSED-LOOP AI-OPTIMIZED EMF TREATMENT AND DIGITAL DELIVERY OF DATA

(71) Applicant: University of Iowa Research Foundation, Iowa City, IA (US)

(72) Inventors: Calvin S. Carter, Iowa City, IA (US); Sunny C. Huang, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1150 days.

(21) Appl. No.: 17/307,830

(22) Filed: May 4, 2021

(65) Prior Publication Data

US 2021/0272664 A1    Sep. 2, 2021

Related U.S. Application Data

(63) Continuation-in-part of application No. 16/947,824, filed on Aug. 19, 2020, now Pat. No. 11,850,440, and
(Continued)

(51) Int. Cl.
*G16H 20/00* (2018.01)
*A61B 5/145* (2006.01)
(Continued)

(52) U.S. Cl.
CPC .......... *G16H 20/00* (2018.01); *A61B 5/14532* (2013.01); *A61N 2/004* (2013.01);
(Continued)

(58) Field of Classification Search
CPC .......... A61N 2/00; A61N 2/002; A61N 2/004; A61N 2/006; A61N 2/008; A61N 2/02; A61N 2/06; A61N 2/12
See application file for complete search history.

(56) References Cited

U.S. PATENT DOCUMENTS 3,915,151 A    10/1975    Kraus
4,428,366 A    1/1984    Findl et al.
(Continued)

FOREIGN PATENT DOCUMENTS

EP    1091786 B1    12/2005
WO    WO-02/098501 A2    12/2002
(Continued)

OTHER PUBLICATIONS

"U.S. Appl. No. 16/947,824, Non Final Office Action mailed Jun. 24, 2022", 11 pgs.
(Continued)

*Primary Examiner* — Samuel G Gilbert
(74) *Attorney, Agent, or Firm* — Schwegman Lundberg & Woessner, P.A.

(57) ABSTRACT

A system may include a processor-based system including at least one processor and memory comprising instructions. When executed by the processor-based system, the instructions cause the processor-based system to: access metrics of a subject who is being treated with a therapy that includes a magnetic non-parallel electric field (MNPEF) therapy or a magnetic non-parallel magnetic field (MNPMF) therapy, wherein the accessed metrics include at least one analyte, the at least one analyte including one or more of blood glucose data, lactate data, or pyruvate data, free fatty acid data, cholesterol data, and compliance data for complying with the therapy; use the accessed metrics as an input to a machine learning algorithm that is configured to determine a set of therapy parameters for the therapy, and program a controller operably connected to at least one energy field system to deliver the therapy according to the determined set of therapy parameters.

22 Claims, 5 Drawing Sheets

Related U.S. Application Data a continuation-in-part of application No. 16/280,551, filed on Feb. 20, 2019, now Pat. No. 11,071,875.

(60) Provisional application No. 63/019,677, filed on May 4, 2020, provisional application No. 62/890,372, filed on Aug. 22, 2019, provisional application No. 62/632,540, filed on Feb. 20, 2018.

(51) Int. Cl.
*A61N 2/00* (2006.01)
*G06N 20/00* (2019.01)
*G16H 10/60* (2018.01)
*G16H 80/00* (2018.01)

(52) U.S. Cl.
CPC ............ *G06N 20/00* (2019.01); *G16H 10/60* (2018.01); *G16H 80/00* (2018.01)

(56) References Cited

U.S. PATENT DOCUMENTS

| | | |
|---|---|---|
| 4,556,051 A | 12/1985 | Maurer |
| 4,838,850 A | 6/1989 | Rosengart |
| 4,850,959 A | 7/1989 | Findl |
| 5,267,152 A | 11/1993 | Yang et al. |
| 5,267,252 A | 11/1993 | Amano |
| 5,803,896 A | 9/1998 | Chen |
| 6,048,302 A * | 4/2000 | Markoll .................. A61N 2/02 600/13 |
| 6,210,317 B1 | 4/2001 | Bonlie |
| 6,418,345 B1 | 7/2002 | Tepper et al. |
| 6,443,883 B1 | 9/2002 | Ostrow et al. |
| 6,652,444 B1 | 11/2003 | Ross |
| 6,751,506 B2 | 6/2004 | Shealy |
| 6,856,839 B2 | 2/2005 | Litovitz |
| 8,700,161 B2 | 4/2014 | Harel et al. |
| 8,825,174 B2 | 9/2014 | Panting |
| 9,320,913 B2 | 4/2016 | Dimino et al. |
| 9,327,136 B2 | 5/2016 | Hedgecock |
| 11,071,875 B2 * | 7/2021 | Carter .............. A61N 1/36034 |
| 11,850,440 B2 * | 12/2023 | Carter .................... A61N 2/004 |
| 2001/0044643 A1 | 11/2001 | Litovitz |
| 2002/0198567 A1 | 12/2002 | Keisari et al. |
| 2003/0055464 A1 | 3/2003 | Darvish et al. |
| 2004/0176805 A1 | 9/2004 | Whelan et al. |
| 2005/0197522 A1 | 9/2005 | Pilla |
| 2005/0215842 A1 | 9/2005 | Pilla et al. |
| 2005/0267535 A1 | 12/2005 | Tofani |
| 2006/0167499 A1 | 7/2006 | Palti |
| 2007/0173889 A1 | 7/2007 | Rosenspire et al. |
| 2008/0057556 A1 | 3/2008 | Miyakoshi et al. |
| 2008/0087288 A1 | 4/2008 | Wun |
| 2009/0131993 A1 | 5/2009 | Rousso et al. |
| 2010/0197993 A1 | 8/2010 | Vasishta |
| 2011/0105828 A1 | 5/2011 | Perless et al. |
| 2011/0230939 A1 | 9/2011 | Weinstock |
| 2012/0302821 A1 | 11/2012 | Burnett |
| 2013/0178910 A1 | 7/2013 | Azamian et al. |
| 2014/0194668 A1 | 7/2014 | Hanson |
| 2014/0296948 A1 | 10/2014 | Sluijter |
| 2014/0357935 A1 | 12/2014 | Ilmoniemi et al. |
| 2016/0129273 A1 | 5/2016 | Park |
| 2017/0156662 A1 * | 6/2017 | Goodall ................. A61N 2/002 |
| 2018/0221656 A1 | 8/2018 | Garcia Perez et al. |
| 2019/0126036 A1 | 5/2019 | Franco-obregon et al. |
| 2019/0255344 A1 | 8/2019 | Carter et al. |
| 2021/0052910 A1 | 2/2021 | Carter et al. |

FOREIGN PATENT DOCUMENTS

| | | |
|---|---|---|
| WO | WO-2008/019710 A1 | 2/2008 |
| WO | WO-2009/061142 A2 | 5/2009 |
| WO | WO-2009/090440 A1 | 7/2009 |
| WO | WO-2010/067180 A2 | 6/2010 |
| WO | WO-2012/083259 A2 | 6/2012 |
| WO | WO-2014/070287 A1 | 5/2014 |
| WO | WO-2015/069446 A1 | 5/2015 |
| WO | WO-2019/164903 A1 | 8/2019 |

OTHER PUBLICATIONS

"U.S. Appl. No. 16/947,824, Response filed Dec. 14, 2022 to Non Final Office Action mailed Jun. 24, 2022", 12 pgs.

"U.S. Appl. No. 16/947,824, Final Office Action mailed Apr. 11, 2023", 17 pgs.

"U.S. Appl. No. 16/947,824, Response filed Jul. 11, 2023 to Final Office Action mailed Apr. 11, 2023", 16 pgs.

"U.S. Appl. No. 16/947,824, Notice of Allowance mailed Aug. 11, 2023", 9 pgs.

"U.S. Appl. No. 16/280,551, Non-Final Office Action mailed Dec. 11, 2020", 16 pgs.

"U.S. Appl. No. 16/280,551, Notice of Allowance mailed Mar. 24, 2021", 11 pgs.

"U.S. Appl. No. 16/280,551, Response filed Mar. 11, 2021 to Non-Final Office Action mailed Dec. 11, 2020", 10 pgs.

"Australian Application Serial No. 2019223992, First Examination Report mailed Mar. 6, 2021", 6 pgs.

"Effect of Intensive Therapy on Residual B-Cell Function in Patients with Type 1 Diabetes in the Diabetes Control and Complications Trial—a Randomized, Controlled Trial", Annals of Internal Medicine, 128(7), (1998), 517-523.

"European Application Serial No. 19709259.6, Response filed Mar. 23, 2021 to Communication pursuant to Rules 161(2) and 162 EPC", 30 pgs.

"Far Infrared Radiation Treatment for Diabetes", [online], Retrieved from the Internet: <URL: https://clinicaltrials.gov/ct2/show/NCT00573456>, (Aug. 2009), 5 pgs.

"Guidance for Industry—Diabetes Mellitus: Developing Drugs and Therapeutic Biologics for Treatment and Prevention", U. S. Department of Health and Human Services, Food and Drug Administration, (Feb. 2008), 34 pgs.

"International Application Serial No. PCT/US2019/018716, International Preliminary Report on Patentability mailed Sep. 3, 2020", 9 pgs.

"International Application Serial No. PCT/US2019/018716, International Search Report mailed Jun. 6, 2019", 6 pgs.

"International Application Serial No. PCT/US2019/018716, Written Opinion mailed Jun. 6, 2019", 9 pgs.

Ahmad, Waqar, et al., "Oxidative toxicity in diabetes and Alzheimer's disease: mechanisms behind ROS/RNS generation", Journal of Biomedical Science, 24: 76, (2017), 1-10.

Alfaras, Irene, et al., "Health benefits of late-onset metformin treatment every other week in mice", npj Aging and Mechanisms of Disease, 3: 16, (2017), 1-13.

Barber, Sian, et al., "Oxidative stress in ALS: Key role in motor neuron injury and therapeutic target", Free Radical Biology & Medicine, 48, (2010), 629-641.

Birch-Machin, Mark A., et al., "An Evaluation of the Measurement of the Activities of Complexes I-IV in the Respiratory Chain of Human Skeletal Muscle Mitochondria", Biochemical Medicine and Metabolic Biology, 51, (1994), 35-42.

Blaser, Heiko, et al., "TNF and ROS Crosstalk in In?ammation", Trends in Cell Biology, 26(4), (Apr. 2016), 249-261.

Bouzid, Mohamed A., et al., "Radical Oxygen Species, Exercise and Aging: an Update", Sports Med, 45, (2015), 1245-1261.

Buckingham, Bruce, et al., "Effectiveness of Early Intensive Therapy on B-Cell Preservation in Tpe 1 Diabetes", Diabetes Care. published online Oct. 15, 2013, (2013), 1-6.

Caduff, A., et al., "First human experiments with a novel non-invasive, non-optical continuous glucose monitoring system", Biosensors & Bioelectronics, 19(3), (2003), 209-217.

Carter, Calvin S., et al., "Abnormal development of NG2+PDGFR-a+ neural progenitor cells leads to neonatal hydrocephalus in a cillopathy mouse model", Nature Medicine, 18(12), (2012), 1797-1804 (9 pgs.).

(56) References Cited

OTHER PUBLICATIONS

Cox, Carly S., et al., "Mitohormesis in Mice via Sustained Basal Activation of Mitochondrial and Antioxidant Signaling", Cell Metab., 28(5), (2018), 776-786.
Curry, Daniel W., et al., "Targeting AMPK Signaling as a Neuroprotective Strategy in Parkinson's Disease", Journal of Parkinson's Disease, 8, (2018), 161-181.
De Haes, Wouter, et al., "Metformin promotes lifespan through mitohormesis via the peroxiredoxin PRDX-2", Proc. of the Natl. Acad. Sci. USA, 111, (2014), E2501-E2509.
Devos, David, et al., "Targeting Chelatable Iron as a Therapeutic Modality in Parkinson's Disease", Antioxidants & Redox Signaling, 21(2), (2014), 195-210.
Dugan, Laura L., et al., "AMPK dysregulation promotes diabetes-related reduction of superoxide and mitochondrial function", The Journal of Clinical Investigation, vol. 123, No. 11, (Nov. 2013), 4888-4899.
El-Kenawi, Asmaa, et al., "Inflammation, ROS, and Mutagenesis", Cancer Cell, 32, (2017), 727-729.
Finkel, Toren, "Signal transduction by reactive oxygen species", J. Cell Biol., 194(1), (2011), 7-15.
Fisher-Wellman, Kelsey H., et al., "Linking mitochondrial bioenergetics to insulin resistance via redox biology", Trends in Endocrinology and Metabolism, 23(3), (Mar. 2012), 142-153.
Foretz, Marc, et al., "Metformin inhibits hepatic gluconeogenesis in mice independently of the LKB1/AMPK pathway via a decrease in hepatic energy state", The Journal of Clinical Investigation, 120(7), (Jul. 2010), 2355-2369.
Furman, Brian L., et al., "Streptozotocin-Induced Diabetic Models in Mice and Rats", Curr. Protoc. Pharmacol., Suppl. 70, (Sep. 2015), 5.47.1-5.47.20.
Glasauer, Andrea, et al., "Targeting antioxidants for cancer therapy", Biochemical Pharmacology, 92, (2014), 90-101.
Havas, Magda, "Dirty Electricity Elevates Blood Sugar Among Electrically Sensitive Diabetics and May Explain Brittle Diabetes", Electromagnetic Biology and Medicine, 27, (2008), 135-146.
Hwang, Onyou, et al., "Role of Oxidative Stress in Parkinson's Disease", Experimental Neurobiology, 22(1), (2013), 11-17.
Jin, Huajun, et al., "Mitochondria-Targeted Antioxidants for Treatment of Parkinson's Disease: Preclinal and Clinical Outcomes", NIH Public Access, Author manuscript, published in final edited form as: Biochim Biophys Acta., 1842(8), (2014), 1282-1294, (2014), 33 pgs.
Keymeulen, B., et al., "Four-year metabolic outcome of a randomised controlled CD3-antibody trial in recent-onset type 1 diabetic patients depends on their age and baseline residual beta cell mass", Diabetologia, 53, (2010), 614-623.
King, Aileen J. F., et al., "The use of animal models in diabetes research", British Journal of Pharmacology, 166, (2012), 877-894.
Kirillov, I. B., et al., "[Magentotherapy in the comprehensive treatment of vascular complications of diabetes mellitus]", Klin Med (Mosk), 74(5), (1996), 39-41, (1996), 1 pg.
Kobayashi, Kunihisa, et al., "The db/db Mouse, a Model for Diabetic Dyslipidemia: Molecular Characterization and Effects of Western Diet Feeding", Metabolism, 49(1), (2000), 22-31.
Kumar, Anil, et al., "A review on mitochondrial restorative mechanism of antioxidants in Alzheimer's disease and other neurological condictions", Frontiers in Pharmacology, vol. 6, Article 206, (Sep. 2015), 1-13.
Lark, D. S., et al., "Enhanced Mitochondrial Superoxide Scavenging Does Not Improve Muscle Insulin Action in the High Fat-Fed Mouse", PLoS ONE 10(5): e0126732, (2015), 1-11.
Lee, Sihoon, et al., "Comparison between surrogate indexes of insulin sensitivity and resistance and hyperinsulinemic euglycemic clamp estimates in mice", Am J Physiol Endocrinol Metab, 294, (2008), E261-E270.
Leloup, Corinne, et al., "Mitochondrial Reactive Oxygen Species Are Obligatory Signals for Glucose-Induced Insulin Secretion", Diabetes, vol. 58, (Mar. 2009), 673-681.

Liochev, Stefan I., et al., "Reactive oxygen species and the free radical theory of aging", Free Radical Biology and Medicine, 60, (2013), 1-4.
Livingstone, Shona J., et al., "Estimated Life Expectancy in a Scottish Cohort With Type 1 Diabetes, 2008-2010", JAMA, 313(1), (2015), 37-44.
Loh, Kim, et al., "Reactive Oxygen Species Enhances Insulin Sensitivity", Cell Metabolism, 10, (2009), 260-272.
Luna-Lopez, Armando, et al., "New considerations on hormetic response against oxidative stress", J. Cell Commun. Signal, 8(4), (2014), 323-331.
Madiraju, Anila K., et al., "Metformin suppresses gluconeogenesis by inhibiting mitochondrial glycerophosphate dehydrogenase", Nature, 510, (2014), 542-546 (17 pgs.).
Mahadev, Kalyankar, et al., "The NAD(P)H Oxidase Homolog Nox4 Modulates Insulin-Stimulated Generation of H2O2 and Plays an Integral Role in Insulin Signal Transduction", Molecular and Cellular Biology, 24(5), (Mar. 2004), 1844-1854.
Markesbery, William R., "The Role of Oxidative Stess in Alzheimer's Disease", Arch Neurol, 56, (1999), 1449-1452.
Martin-Montalvo, Alejandro, et al., "Metformin improves healthspan and lifespan in mice", HHS Public Access, Author manuscript, published in final edited form as: Nat Commun., 4, (2013), 2192, (2013), 23 pgs.
Mittal, Manish, et al., "Reactive Oxygen Species in Inflammation and Tissue Injury", Antioxidants & Redox Signaling, 20(7), (2014), 1126-1167.
Mogavero, Angelo, et al., "Metformin transiently inhibits colorectal cancer cell proliferation as a result of either AMPK activation or increased ROS production", Scientific Reports, 7: 15992, (2017), 1-12.
Owen, Mark R., et al., "Evidence that metformin exerts its anti-diabetic effects through inhibition of complex 1 of the mitochondrial respiratory chain", Biochem. J., 348, (2000), 607-614.
Poprac, Patrik, et al., "Targeting Free Radicals in Oxidative Stress-Related Human Diseases", Trends in Pharmacological Sciences, 38(7), (Jul. 2017), 592-607.
Puspita, Lesly, et al., "Oxidative stress and cellular pathologies in Parkinson's disease", Molecular Brain, 10: 53, (2017), 12 pgs.
Qinna, Nidal A., et al., "Impact of streptozotocin on altering normal glucose homeostasis during insulin testing in diabetic rats compared to normoglycemic rats", Drug Design, Development and Therapy, 9, (2015), 2515-2525.
Radak, Zsolt, et al., "Exercise and hormesis: oxidative stress-related adaptation for successful aging", Biogerontology, 6, (2005), 71-75.
Raza, Muhammad H., et al., "ROS-modulated therapeutic approaches in cancer treatment", J. Cancer Res Clin Oncol, 143, (2017), 1789-1809.
Sherifali, Diana, et al., "The Effect of Oral Antidiabetic Agents on Glycated Hemoglobin Levels: a Systematic Review and Meta-Analysis", Diabetes Care, (2010), 1-11.
Sieron, A., "Effect of Low Frequency Electromagnetic Fields on [3H]Glucose Uptake in Rat Tissues", Polish J. of Environ. Stud., 16(2), (2007), 309-312.
Simm, Andreas, et al., "Reactive oxygen species (ROS) and aging: Do we need them can we measure them should we block them?", Signal Transduction, 3, (2005), 115-125.
Song, Chang W., et al., "Metformin kills and radiosensitizes cancer cells and preferentially kills cancer stem cells", Scientific Reports, 2: 362, (2012), 1-9.
Steffes, Michael W,, et al., "B-Cell Function and the Development of Diabetes-Related Complications in the Diabetes Control and Complications Trial", Diabetes Care, 26(3), (Mar. 2003), 832-836.
Tonnies, Eric, et al., "Oxidative Stress, Synaptic Dysfunction, and Alzheimer's Disease", Journal of Alzheimer's Disease, 57, (2017), 1105-1121.
Valencia, Willy M., et al., "Metformin and ageing: improving ageing outcomes beyond glycaemic control", HHS Public Access, Author manuscript, published in final edited form as: Diabetologia, 60(9), (2017), 1630-1638, (2017), 16 pgs.
Vetere, Amedeo, et al., "Targeting the pancreatic β-cell to treat diabetes", Nature Reviews Drug Discovery, 13, (Aoeil 2014), 278-289.

(56) References Cited

OTHER PUBLICATIONS

Wang, G, J., et al., "Low-dose radiation and its clinical implications: diabetes", Hum Exp Toxicol, 27(2), (2008), 135-142.

Wang, Huizhen, et al., "Magnetic Fields and Reactive Oxygen Species", Int. J. Mol. Sci., 18, 2175, (2017), 20 pgs.

Wang, Jian, "Mitochondria as a therapeutic target in Alzheimer's disease", Genes & Diseases, 3, (2016), 220-227.

Wheaton, William W., et al., "Metformin inhibits mitochondrial complex I of cancer cells to reduce tumorigenesis", eLife, 3:e02242, (2014), 18 pgs.

Yang, Xiangjun, et al., "Antioxidant Treatment Limits Neuroin?ammation in Experimental Glaucoma", IOVS, 57(4), (Apr. 2016), 2344-2354.

Zhang, Hui-Hui, et al., "Combinational strategies of metformin and chemotherapy in cancers", Cancer Chemother Pharmacol, 78, (2016), 13-26.

\* cited by examiner

CLOSED-LOOP AI-OPTIMIZED EMF TREATMENT AND DIGITAL DELIVERY OF DATA

CLAIM OF PRIORITY

This application claims the benefit of priority under 35 U.S.C. § 119(e) of U.S. Provisional Patent Application Ser. No. 63/019,677, filed on May 4, 2020, and titled "CLOSED-LOOP AI-OPTIMIZED EMF TREATMENT AND DIGITAL DELIVERY OF DATA", which is incorporated by reference herein in its entirety.

This application is a continuation-in-part application of U.S. application Ser. No. 16/280,551, filed Feb. 20, 2019, published as U.S. Publication Number 20190255344A1, and titled "THERAPEUTIC SYSTEMS USING MAGNETIC AND ELECTRIC FIELDS," which claims the benefit of priority under 35 U.S.C § 119(e) of U.S. Provisional Patent Application Ser. No. 62/632,540, filed on Feb. 20, 2018, and titled "TREATMENT OF DIABETES USING MAGNETIC AND NON-PARALLEL ELECTROSTATIC FIELDS," each of which are herein incorporated by reference in their entirety.

This application is a continuation-in-part application of U.S. application Ser. No. 16/947,824, filed Aug. 19, 2020, published as U.S. Publication Number 20210052910A1, and titled "THERAPEUTIC SYSTEMS USING MAGNETIC FIELDS," which claims the benefit of priority under 35 U.S.C. § 119(e) of U.S. Provisional Patent Application Ser. No. 62/890,372, filed on Aug. 22, 2019, and titled "THERAPEUTIC SYSTEMS USING MAGNETIC FIELDS," each of which are herein incorporated by reference in their entirety.

STATEMENT OF GOVERNMENT INTEREST

This invention was made with government support under 1RO1 NS083543 awarded by the National Institutes of Health. The government has certain rights in the invention.

TECHNICAL FIELD

The present disclosure relates generally to medical systems, and more particularly, to systems, devices, and methods for delivering therapy by delivering energy to tissue.

BACKGROUND

Existing therapies for chronic diseases, such as but not limited to diabetes, cancer, neurological and immune diseases, have significant challenges. For example, existing therapies may only treat symptoms of the disease, may be invasive, and/or may have relatively low patient adherence.

By way of a non-limiting example, many diabetic patients have failed to achieve a healthy glycemic range and have a significantly greater risk of premature death in spite of the medications that are available to manage the disease. Patients may fail to adhere to their therapy because of the complexity of the dosing regimen for their prescribed medication, the discomfort of testing and insulin injections, and drug intolerability. Conventional diabetic care and the cost of treating complications resulting from poorly-managed diabetes is very expensive for individuals and the healthcare system at large.

What is needed is an improved therapy for treating chronic diseases that addresses some of these shortcomings of existing therapies.

SUMMARY

This Summary includes examples that provide an overview of some of the teachings of the present application and is not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (of subject matter (such as a system, a device, apparatus or machine) may be used with a magnetic non-parallel electric field (MNPEF) or magnetic non-parallel magnetic field (MNPMF) therapy, and may comprise a processor-based system including at least one processor and memory comprising instructions. When executed by the processor-based system, the instructions cause the processor-based system to: access metrics of a subject who is being treated with the MNPEF or MNPMF therapy, wherein the accessed metrics may include at least one analyte (e.g., one or more of blood glucose data, lactate data, pyruvate data, free fatty acid data, or cholesterol data), and compliance data for complying with an MNPEF or MNPMF therapy; use the accessed metrics as an input to a machine learning algorithm that is configured to determine a set of therapy parameters for the MNPEF or MNPMF therapy based on the accessed metrics; and program the MNPEF or MNPMF therapy using the determined set of therapy parameters. The machine learning algorithm being configured to continually improve a model for determining the set of therapy parameters based on the accessed metrics.

An example of subject matter (such as a method, means for performing acts, machine readable medium including instructions that when performed by a machine cause the machine to perform acts, or an apparatus to perform). The subject matter may include using a processor-based system that includes at least one processor to access metrics of a subject who is being treated with a magnetic non-parallel electric field (MNPEF) or magnetic non-parallel magnetic field (MNPMF) therapy. The accessed metrics may include at least one analyte (e.g., one or more of blood glucose data, lactate data, pyruvate data, free fatty acid data, or cholesterol data) and compliance data for complying with an MNPEF or MNPMF therapy. The subject matter may further use the processor-based system to use the accessed metrics as an input to a machine learning algorithm that is configured to determine a set of therapy parameters for the MNPEF or MNPMF therapy based on the accessed metrics, and program the MNPEF or MNPMF therapy using the determined set of therapy parameters. The machine learning algorithm being configured to continually improve a model for determining the set of therapy parameters based on the accessed metrics.

An example of subject matter (such as a method, means for performing acts, machine readable medium including instructions that when performed by a machine cause the machine to perform acts, or an apparatus to perform). The subject matter may treat a condition, such as diabetes, cancer, obesity, inflammation, neurodegeneration or glaucoma, using a magnetic non-parallel electric field (MNPEF) or magnetic non-parallel magnetic field (MNPMF) therapy. The subject matter may comprise using a processor-based system that includes at least one processor to access at least one analyte of a subject who is being treated with the MNPEF or MNPMF therapy, and use the at least one analyte as an input to a machine learning algorithm that is configured to determine a set of therapy parameters for the MNPEF or MNPMF therapy based on the at least one analyte. By way of example, analyte may be assessed in whole blood, plasma, serum, red blood cells, tears, urine, stool, cerebrospinal fluid, or lymphatic fluid. The machine learning algorithm being configured to continually improve a model for determining the set of therapy parameters based on the at least one analyte. The subject matter may program the MNPEF or MNPMF therapy using the determined set of therapy parameters. The analyte may be indicative of therapy efficacy, and may include one or more biomarkers within at least one of a redox system and a metabolic system. The one or more biomarkers may include glutathione (GSH), glutathione disulfide (GSSG), cysteine (Cys), cystine (CysS), protein S-glutathionylation (PrSSG), protein S-cysteinylation (PrCysS), a redox potential of glutathione (GSH), a redox potential of glutathione disulfide (GSSG), a redox potential of cysteine (Cys), a redox potential of cystine (CysS), F2-isoprostane, at least one biomarker of glucose metabolism, lipid peroxidation or oxidative stress, glucose, insulin, glucagon, HbA1c, glycogen, c-peptide, pyruvate, lactate, FGF21, GDF15, adiponectin, respiratory quotient (RQ), iron, ferritin, aconitate, hemoglobin, total iron-binding capacity, transferrin, transferrin saturation, hepcidin, ferroportin, heme, transferrin receptor, albumin, platelet count, clotting factors, bilirubin, aspartate transaminase (AST), alanine aminotransferase (ALT), gases (e.g. $CO_2$, $O_2$, $N_2$), pH, folate, ascorbate, glucose-6-phosphate, ribose-5-phosphate, ribulose-5-phosphate, xylulose-5-phosphate, vitamin B12, homocysteine, glutamine, glutamate, aspartate, 2-oxoglutarate, glycine, high density lipoprotein (HDL), low density lipoprotein (LDL), very low density lipoprotein(VLDL), triglycerides, malondialdehyde (MDA), cholesterol, lipocalin, orosomucoid, serum amyloid protein, apolipoprotein, acetyl coA carboxylase, protein kinase AMP-activated protein kinase, carbohydrate response element binding protein, sterol regulatory element-binding protein, peroxisome proliferator-activated receptor, uncoupling protein, dopanmine, serotonin, c-reactive protein, interleukins, tumor necrosis factor, immunoglobulin, complement factors, matrix metalloproteinases, bile acids (primary and secondary) or cortisol. The one or more biomarkers may include a product of free radical mediated oxidation of arachidonic acid, at least one antioxidant from thioredoxin (Trx), peroxiredoxin (Prdx), glutathione-S-transferase (GST), or glutathione peroxidase 3 (GPX3), an expression of genes that induce the antioxidant response, including NRF2, an expression of genes that are activated by NRF2 to mediate the antioxidant response, including at least one of: NAD(P)H dehydrogenase [quinone]1 (NQO1) heme oxygenase 1 (HMOX1), glutamate-cysteine ligase catalytic subunit (GCLC), glutamate-cysteine ligase regulatory subunit (GCLM) (see Kansanen et al.), the redox couples, NADP+, NA)PH, NAD+, NADH, redox post-translational modifications, long-chain fatty acids (LCFAs) (e.g. myristate, myristoleate, pentadecanoate, palmitate, palmitoleate, margarate, 10-heptadecanoate, stearate, oleate, vaccinate, nonadecanoate, 10-nonadecenoate, arachidate, eicosanoate, educate etc.), poly unsaturated fatty acids (PUFAs) (e.g. heneicosapentaenoate, tetradecadienoate, hexadecadienoate, hexadecatrienoate, stearidonate, eicosapentaenoate, docasapentaenoate, docosahexaenoate, docosatrienoate, nisinate, linoleate, linolenate, dihomo-linolenate, arachidonate, adrenate, docosapentaenoate, docosadienoate, dihomo-linoleate, mead acid, docosatrienoate), medium chain fatty acids (MCFAs) (e.g. heptanoate, cis-4-decenoate, 10-undecenoate, 5-dodecenoate etc.), fatty acids dicarboxylate (e.g. glutarate, 2-hydroxyglutarate, 2-hydroxyadipate, 3-hydroxyadipate, suberate, azelate, sebacate, dodecadienoate, dodecanedioate, tetradecanedioate, hexadecanedioate, octadecenedioate, tetradecadienedioate, 3-carbodyy-4-methyol-5-propyl-2-furanpropanoate, 3-carboxy-4-methyl-5-pentyl-2-furanpropionate etc.), amino fatty acids (e.g. 2-aminoheptanoate, 2-aminooctanoate, n-acetyl-2-aminooctanoate etc.), acyl glycine (e.g. isocaproylglycine, valerylglycine, hexanoylglycine, 4-methyihexanoyigiycine, trans-2-hexanoylglycine, n-octanoylglycine, 2-butanoylglycine, 3-hydroxybutyroylglycine etc.) and carnitines (e.g. acetylcarnitine, (R)-3-hydroxybutyrylcarnitine, hexanoylcarnitine, octanoylcarnitine, decanoylcarnitine, 5-dodecenoylcarnitine, cis-4-decenoylcarnitine, laurylcarnitine, myristoylcarnitine, palmitoylcarnitine palmitoleoylcarnitine, stearoylcarnitine, linoleoylcarnitine, linolenoylcarnitine, 3-hydroxyoleoylcarnitine, oleoylcarnitine, myristoleoylcarnitine, adipoylcarnitine, octadecenedioylcarnitine, arachidoylcarnitine, arachidonoylearnitine, behenoylcarnitine, dihonio-linolenoylcarnitine, dihomo-linoleoylcarnitine, eicosenoylcarnitine, docosahexaenoylcarnitine, lignoceroylcarnitine, nervonoylcarnitine, margaroylcarnitine, pentadecanoylcarnitine, 3-hydroxypalmitoylcarnitine, deoxycarnitine, carnitine etc.) or beta-hydroxybutyrate. The one or more biomarkers may include a redox potential, GSH, glutathionylation, cysteinylation, or NRF2. The one or more biomarkers may be detected in whole blood, plasma, serum, red blood cells, tears, urine, stool, cerebrospinal fluid, or lymphatic fluid.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
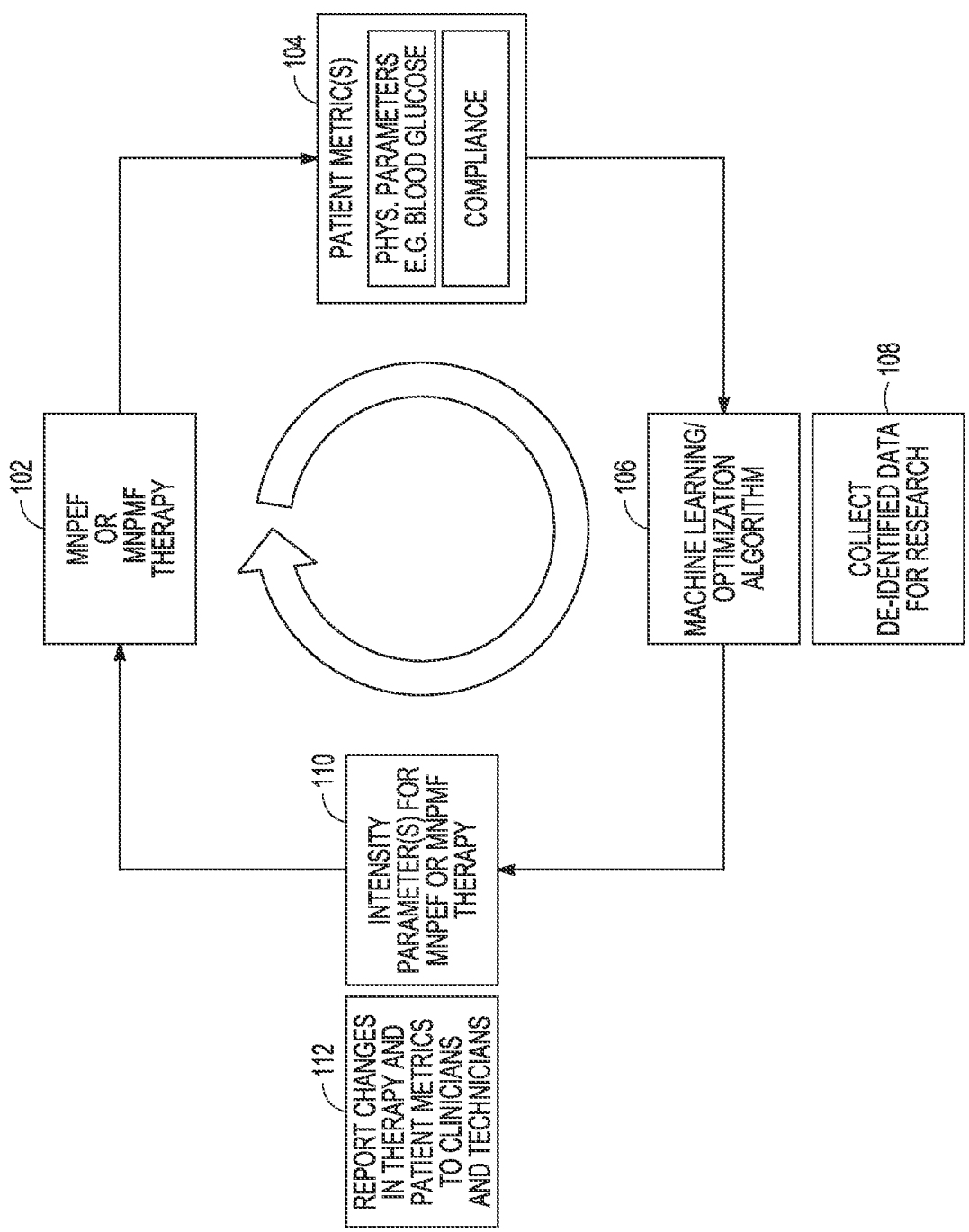
FIG. 1 illustrates, by way of example and not limitation, an embodiment of data and control flow in a closed-loop system that utilizes artificial intelligence/machine learning algorithms.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

According to various embodiments discussed herein, data regarding patient treatment parameters and patient health characteristics is collected and processed using machine learning algorithms driven by artificial intelligence (AI) for the optimization of the therapy (MNPEF or MNPMF). Data may be delivered to patients and physicians regarding compliance, treatment efficacy and device usage. The machine learning algorithms driven by artificial intelligence attempt to optimize the efficacy of the therapy for the patient and for future patients who share similar characteristics that correspond with a positive treatment response.

The MNPEF/MNPMF may be paired with continuous glucose monitoring or monitoring of the redox state (the systemic levels of oxidants and antioxidants or the levels of oxygen) for the closed loop control of blood glucose and the systemic redox state (plasma levels of oxidants e.g., $H_2O_2$, superoxide, hydroxyl and hydroxide and antioxidants which entails the redox couples, GSH/GSSG, CyS, CysS, the thioredoxin and peroxiredox systems). Data, such as data regarding adherence, device contact, pressure activation, psychophysiological measures, patient characteristics (such as but not limited to height, weight, BMI, ethnicity, age, glucose, A1c, insulin dose, oxidant levels, antioxidant levels), oxygen saturation, may be provided to physicians and patients via a mobile app or integration with digital systems. Machine learning algorithms may be implemented to predict treatment efficacy, optimization of therapy and personalization of therapy. The present subject matter provides a minimally invasive closed loop system for the noninvasive management of chronic disease, patient adherence and education to patients and physicians, and further provides non-invasive support for disease management.

The present subject matter may use artificial intelligence, or machine learning as a form of artificial intelligence that may use iterative processes to improve associations between or among data. Machine learning may be used to develop and continually improve the models, as a machine learning model may be trained on data and then can be used to learn from data.

Machine-learning programs (MLPs), also referred to as machine-learning algorithms or tools, may be used to perform operations associated with machine learning tasks, such as identifying relationship(s) between detected metrics of a subject and parameters for delivering a therapy.

Machine learning is a field of study that gives computers the ability to learn without being explicitly programmed. Machine learning explores the study and construction of algorithms that may learn from existing data and make predictions about new data. Such machine-learning tools operate by building a model from example training data in order to make data-driven predictions or decisions expressed as outputs or assessments. The machine-learning algorithms utilize the training data to find correlations among identified features that affect the outcome.

The machine-learning algorithms use features for analyzing the data to generate assessments. A feature is an individual measurable property of a phenomenon being observed. Examples of features may include blood glucose, therapy compliance data, A1c (HbA1c), and other patient metrics. The machine-learning algorithms use the training data to find correlations among the identified features that affect the outcome or assessment. With the training data and the identified features, the machine-learning tool is trained. The machine-learning tool appraises the value of the features as they correlate to the training data. The result of the training is a trained machine-learning program.

Machine learning techniques train models to accurately make predictions on data fed into the models. During a learning phase, the models are developed against a training dataset of inputs to optimize the models to correctly predict the output for a given input. Generally, the learning phase may be supervised, semi-supervised, or unsupervised; indicating a decreasing level to which the "correct" outputs are provided in correspondence to the training inputs. In a supervised learning phase, all of the outputs are provided to the model and the model is directed to develop a general rule or algorithm that maps the input to the output. In contrast, in an unsupervised learning phase, the desired output is not provided for the inputs so that the model may develop its own rules to discover relationships within the training dataset. In a semi-supervised learning phase, an incompletely labeled training set is provided, with some of the outputs known and some unknown for the training dataset.

Models may be run against a training dataset for several epochs (e.g., iterations), in which the training dataset is repeatedly fed into the model to refine its results. For example, in a supervised learning phase, a model is developed to predict the output for a given set of inputs, and is evaluated over several epochs to more reliably provide the output that is specified as corresponding to the given input for the greatest number of inputs for the training dataset. In another example, for an unsupervised learning phase, a model is developed to cluster the dataset into n groups, and is evaluated over several epochs as to how consistently it places a given input into a given group and how reliably it produces the n desired clusters across each epoch.

Once an epoch is run, the models are evaluated and the values of their variables are adjusted to attempt to better refine the model in an iterative fashion. In various aspects, the evaluations are biased against false negatives, biased against false positives, or evenly biased with respect to the overall accuracy of the model.

Model training may include an optimization process (e.g., gradient descent), in which a parameter (e.g., a structural element such as a node in a layer of a neural network, or a weight factor associated with the node) is adjusted until a desirable performance is achieved (e.g., minimizing a loss function). In a gradient descent technique, for example a gradient (e.g., partial derivative) is computed to provide a direction, and possibly a degree, of correction. Via several iterations, the parameter will move towards an operationally useful value. That is, the gradient descent method may be used to move a parameter in a direction that produces a better result and away from the direction that produces a worse result. In some implementations, the amount, or step size, of movement is fixed (e.g., the same from iteration to iteration). Small step sizes tend to take a long time to converge, whereas large step sizes may oscillate around the correct value, or exhibit other undesirable behavior. Variable step sizes may be attempted to provide faster convergence without the downsides of large step sizes. To address being stuck in a local minima, a random selection of a parameter value may be used to escape the local minima.

Machine learning may involve supervised, unsupervised, reinforcement or deep learning. Machine learning may implement, by way of example and not limitation, algorithms such as Bayesian, clustering, decision tree, neural networks, linear regression, and rule-based algorithms. These machine learning algorithms attempt to learn or fit data for use in making predictions. Genetic algorithms also attempt to learn or fit data for making predictions, and thus may be considered to be a form of machine learning. Genetic algorithms are entropy driven rather than mistake driven.

FIG. 1 illustrates, by way of example, an embodiment of data and control flow in a system that utilizes machine learning to optimize MNPEF or MNPMF therapy. Therapy is delivered at 102 using an initial set of parameters. Patient metrics are obtained 104. The patient metrics may be obtained via passive or active participation with the patient. The metrics may include physiological parameters such as blood glucose as determined by a continuous glucose monitor (CGM) and may include compliance metrics indicating the patient's compliance with the therapy. Other patient metrics may include clinical data such as A1c (HbA1c) and/or energy metabolite data, and may include other patient data such as redox status, genetics, weight, height, BMI, blood gases, ethnicity, sex, fat mass, lipid content, muscle mass, age, comorbidities, concurrent medications, sleep quality, brainwaves, heart rate, blood pressure.

The patient may provide the patient metrics passively (e.g., based on sensor data and/or electronic medical records)—without active participation. The patient may manually provide patient metrics. For example, the patient may be prompted (e.g., by a clinician or with an electronic graphical user interface) to provide compliance-related data, glucose measurements, or other patient metrics.

The patient metric(s) are used as input to the machine learning or optimization algorithm 106. Various algorithms may be used, such as genetic algorithms, neural networks, or reinforcement learning strategies (e.g., Q-learning, Temporal Difference learning, or Markov decision processes). At 108, de-identified data may be collected for research. The machine learning or optimization algorithm 106 may determine modifications for one or more therapy parameters at 110 such as parameter to control the therapy intensity, stop times and start times. Intensity-related therapy parameter may include amplitude, frequency, duty cycle therapy duration, selection of source(s), orientation of field vectors, shape of field(s), and the like. Changes in the therapy and/or changes in the patient metrics may be reported to clinicians and technicians 112. Changes in the therapy and/or changes in the patient metrics may be reported to the patient and/or patient caregivers (e.g., parent). The system may implement the MNPEF or MNPMF therapy at 102 using the modified parameter(s).

In addition to genetic algorithms, machine learning algorithms that require large data sets such as neural networks may be employed in a preclinical model to allow a larger parameter space to be explored with more testing time. This information can be used to characterize stimulation parameters and design the optimization algorithm in the clinical system.

The machine learning or optimization algorithm may be a genetic algorithm. Therapy parameters are modulated during the optimization search. An objective function uses patient metrics to evaluate the tested therapy parameters. Based on the objective function values, new stimulation parameters are selected for subsequent testing. The objective function may include several feedback components such as, but not limited to, compliance-related data and blood glucose values and trends of blood glucose values. The objective function may then be customized to fit the needs of individual patients by adjusting the objective function component weights to emphasize one aspect more than the other. The genetic algorithm may seek to minimize the objective function value due to changing the stimulation parameters during the search.

Figure 2:
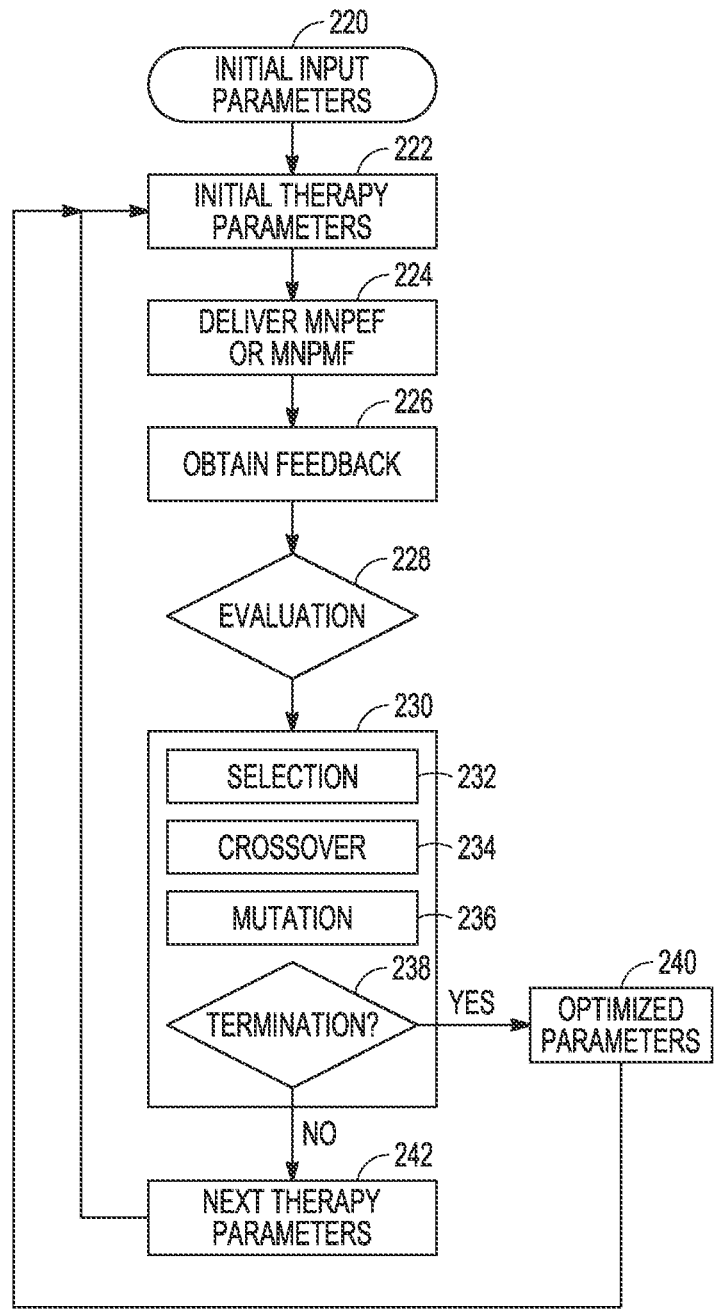
FIG. 2 illustrates, by way of example, another embodiment of data and control flow in a system that utilizes a genetic algorithm as an example of machine learning to optimize neurostimulation patterns.

FIG. 2 illustrates, by way of example, another embodiment of data and control flow in a system that utilizes a genetic algorithm as an example of machine learning to optimize neurostimulation patterns.

At 220 initial input parameters are accessed to determine the initial therapy parameters for the MNPEF or MNPMF therapy. Initial therapy parameters 222 may include one or more of amplitude, frequency, duty cycle therapy duration, therapy schedule (e.g., time of day), selection of source(s), orientation of field vectors, shape of field(s). The initial therapy parameters are used to deliver the MNPEF or MNPMF therapy 224.

At 226, the patient's feedback is received. The patient feedback may include various objective or subjective metrics. Objective metrics may be based on sensor data, electronic medical record chemistries, and subjective patient feedback and may include responses to questionnaires, summaries of diaries, clinician reports, or rating scales.

At 230, the patient's feedback is analyzed to determine whether additional modification to the stimulation parameters is needed. By way of example of a machine learning algorithm and not limitation, a genetic algorithm may be used at to identify one or more stimulation parameters. A genetic algorithm is a general-purpose search algorithm based on the principle of evolution. The population of candidate solutions (called individuals, creatures, or phenotypes) to an optimization problem is evolved toward better solutions. Each candidate solution has a set of properties (its chromosomes or genotype) that can be mutated or altered. A genetic algorithm may combine the operations of selection 232, crossover 234, and mutation 236 with the goal of finding the best solution. The selection-crossover-mutation process favors better solutions from generation to generation. When the genetic algorithm reaches a termination state 238 (e.g., a maximum number of generations) or has convergence to a solution (e.g., minimizes or maximizes an objective function), then the stimulation parameters for optimized therapy are considered to be reached. The optimized therapy parameters 240 may be used until the patient's condition changes or until the parameters are no longer effective. When the genetic algorithm has not reached termination criteria or convergence state, then a next set of therapy parameters is identified and tested 242.

In the selection stage 232, chromosomes of higher fitness are selected to become the co-founders of the next generation of chromosomes. The probability of a chromosome being selected is based on a fitness function. The fitness function is used to choose which chromosomes will be elected to survive to the next generation. The fitness function is a form of an objective function used in machine learning applications. One example design of a fitness function may be to maximize blood glucose values and patient compliance.

The crossover stage 234 is used to select two chromosomes (e.g., parents) and combine them to produce a new chromosome (e.g., offspring). Various crossover techniques may be used, such as one-point crossover, two-point crossover, or a uniform crossover. A one-point crossover function uses a single point in the parent chromosomes, and uses one parent for the first portion of the offspring chromosome and the other parent for the remainder of the offspring chromosome (after the crossover point). A two-point crossover uses two points on the chromosome to create three sections in the offspring chromosome(s), using one parent for the first and third portion of the offspring chromosome and the other parent for the second portion of the offspring chromosome. Crossover points may be chosen randomly or uniformly among chromosomes. Other functions may be used to combine chromosomes. One example function may be to equally weight each gene in the parent chromosomes and randomly select a gene from one parent chromosome for the offspring chromosome.

The mutation stage 236 alters one or more gene values in an offspring chromosome. The gene value may be selected randomly from a chromosome in the general gene pool. The mutated gene value may be constrained to a range (e.g., ±25% of the original gene value). Mutation prevents a selected chromosome population from becoming stagnant.

The termination 238 of the genetic algorithm may be achieved by executing a certain number of iterations (e.g., producing a certain number of generations), or by producing a chromosome that meets a fitness requirement. Other terminating conditions may include reaching an allocated budget (computation time/money), reaching a highest-ranking solution's fitness or reaching a plateau of chromosomes such that successive iterations no longer produce better results, or combinations of these conditions.

Figure 3:
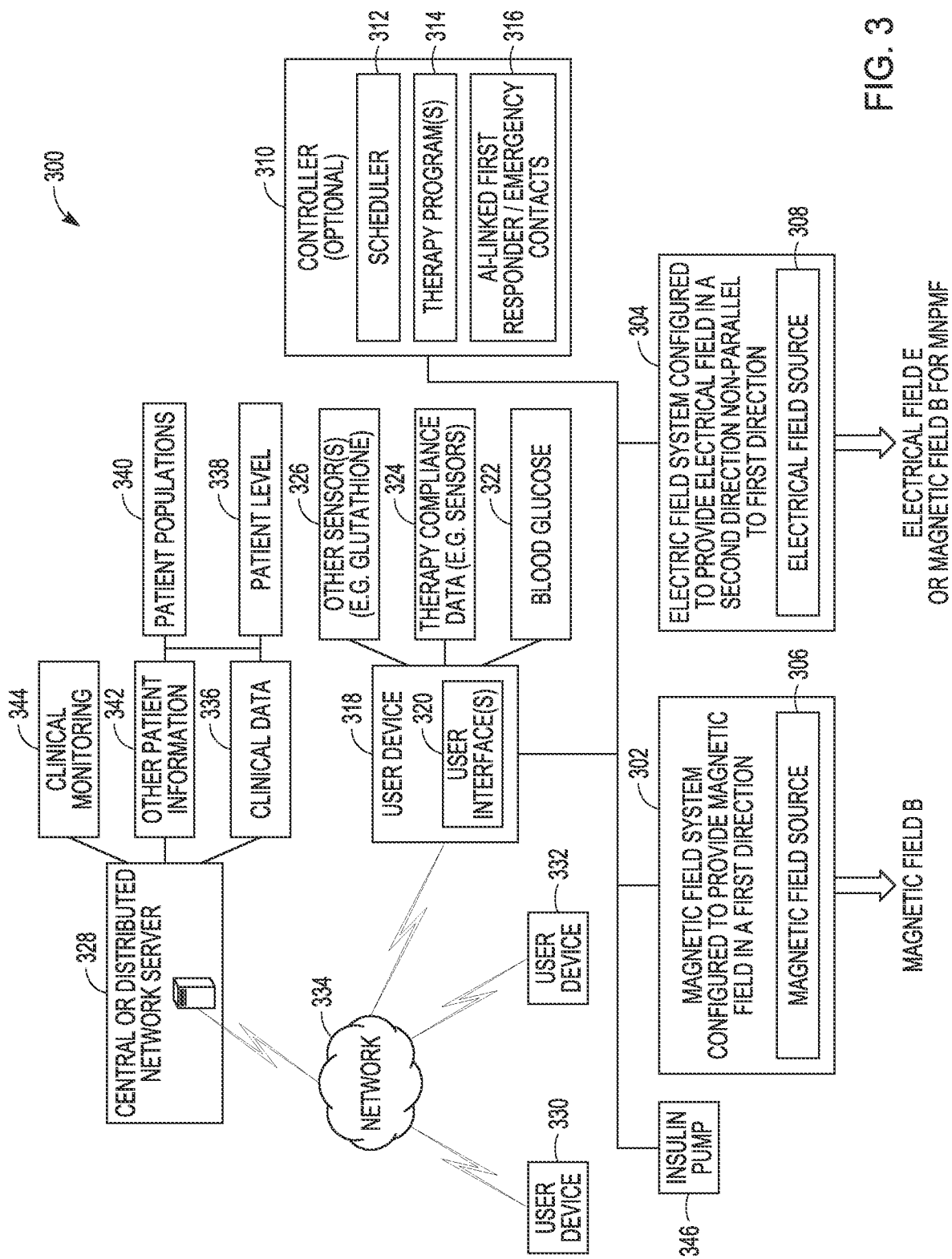
FIG. 3 illustrates, by way of example and not limitation, a system for delivering the closed-loop therapy.

FIG. 3 illustrates, by way of example and not limitation, a system for delivering the closed-loop therapy. The illustrated system 300 includes an energy field system(s) 302 and 304. The magnetic field system 302 may be configured to provide a magnetic field B to targeted tissue, where a vector direction of the magnetic field in the targeted tissue is in at least a first direction. The letter B is conventionally used to denote a magnetic field or flux density. The term "magnetic" is also abbreviated herein with the letter M as used in the MNPMF term. It is noted that the magnetic field may, but need not be, uniform in direction throughout the tissue. That is, the magnetic field may have a complex shape within the tissue, such that the vector direction of the magnetic field within the tissue may vary depending on the position within the tissue. The magnetic field system 302 includes at least one magnetic field source 306 to produce the magnetic field. The magnetic field source(s) 306 may include permanent magnet(s). The magnetic field source(s) 306 may include temporary magnet(s). If a temporary magnet is used, the system will include means to magnetize the temporary magnet via another magnetic source. The magnetic field source(s) 306 may include conductor(s) through which electric current flows to create the magnetic field. The conductor may be a simple wire, a wire loop, or a coil of wire (such as a solenoid). The coil of wire may include a core to enhance the magnetic field generated by the electric current. For example, the magnetic field source(s) may include only one permanent or temporary magnet to produce the magnetic field, and the magnetic field source(s) may include at least two magnets (permanent or temporary), which may be located on opposing sides of the targeted tissue to produce the magnetic field in the first direction to the tissue. More complex arrangements are also contemplated. The magnetic field source(s) may include a conductor which is configured to generate the magnetic field in the first direction to the tissue when current flows through the conductor. The conductor may be a variety of shapes (e.g., line, loop, coil). The conductor may form part of a solenoid. A magnetic core within the coil may be used to strengthen the field. The current in the conductor which forms the magnetic field may be a direct current (DC) or alternating current (AC). Magnetic material with a high magnetic permeability may be used to confine and guide magnetic fields.

The energy field system 304 may be an electric field system, as illustrated, for use to provide MNPEF or another magnetic field system for use to provide MNPMF. The illustrated electric field system 104 includes at least one electric field source 308 to provide the magnetic field in the second direction non-parallel to the first direction. In some embodiments, one magnetic field system may provide the magnetic field(s) in the first and second direction. If the system is designed to deliver MNPMF, then the system 304 will have at least one magnetic field source.

The magnetic/electric field system(s) may be relatively simple systems that are always providing the fields. For example, a system may be designed using permanent magnets. The magnetic field system(s) may be more complex. By way of example, some system embodiments may include sensor(s) that may detect the presence of the patient in an environment (e.g., bed, chair, workstation), and turn on the system in response to detecting the patient's presence near the system. Some embodiments may turn on the system based on a clock/timer (e.g., 10:00 PM), and some embodiments may turn on the system in response to a detecting the patient's presence within a time window (e.g., 10:00 PM to 6:00 AM indicating the patient is in bed, or 9:00 AM to 5:00 PM indicating the patient is at a workstation). Sensor(s) may include a variety of position or motion sensor(s), such as a load sensor to register pressure changes that may be used to detect a patient lying in bed. Sensor(s) may also detect the physiological condition of the patient, which may be used to determine that the patient is in position for the therapy. Other examples may include a temperature sensor, an accelerometer to detect motion or posture, an impedance sensor, a sound sensor, a heart rate sensor, a respiration sensor and activity sensor. FIG. 3 illustrate that the sensors 322, 324 and 326 are connected to the user device. The sensors may be connected to other devices in the system or may be otherwise networked into the illustrated system to allow the system to use the sensed data.

Some system embodiments may include an insulin pump 346, which may be configured to communicate to a specific device in the system or may be configured for network communications to any network devices. The system may be configured to coordinate the MNPEF or MNPMF therapies with the insulin doses provided by the insulin pump 346. Thus, by way of example and not limitation, the system may be configured to recommend and/or control a dose of a long acting (basal) insulin such that the insulin dosing may account for the effectiveness of the MNPEF or MNPMF therapy. The system may be configured to coordinate the MNPEF or MNPMF therapies with chemotherapies, with radiation therapies, with immunotherapies, with antimicrobial therapies, with anti-inflammatory therapies, or with tissue transplantation.

Some system embodiments may include a controller 310 operably connected to at least one of the energy field systems 302 or 304. The controller 310 may include a scheduler 312 configured to control timing for generating at least one of the magnetic fields. The controller 310 may include one or more therapy programs 314 used to generate the MNPMF therapy. Each program may include a set of therapy parameters used to generate the magnetic field(s). The set of therapy parameter(s) may include one or more of an amplitude, frequency, pulse shape or source selection. Each of these therapy parameter(s) may affect the resultant energy fields generated by the energy field system(s). Source selection for the magnetic field system may involve changing a location of a magnet or magnet(s), or energizing different conductor(s) from a plurality of conductors to change the field shape and vector direction of the field. Source selection for the electric field system may involve an array of selectable electrodes to change the shape of the field. Some embodiments may include mechanism(s) to physically move, rotate or re-orientate the energy sources; and the therapy program(s) may implement processes to control those mechanism(s). Various programs may implement protocol(s) to adjust the absolute directions of field vector directions and/or adjust the relative angle between the magnetic field vector directions. The controller 310 may also include first responder or emergency contacts accessible by artificial intelligence 316, enabling the system to communicate directly with the contacts or provide those contacts to system users when the system determines that the first responder or emergency contact should be called or otherwise messaged.

Some system embodiments may include a user device 318 with a user interface 320. The user interface 318 may be configured for use by the user to create and/or modify one or more schedules implemented by the controller 310. The user interface may be configured for use by the user to enter, select or adjust various therapy programs. The therapy parameters nay include amplitude, frequency, pulse shape. Other parameters may include duty cycle, duration, etc. The selectable parameters may include direction (e.g., source selection where selected sources control direction). The user interface may be configured for use by a user to control the start and/or end of the MNPEF or MNPMF therapy or portions thereof (e.g., start and/or stop the energy field(s). The user interface may be configured for use by a user to control motion, rotation or orientation of the source(s) so as to enable user control of the absolute directions of field vector directions and/or the relative angle of the magnetic field vector directions. The start/stop control may be provided using, by way of example and not limitation, a mechanical button or switch or a selectable graphical user element on a display of the controller. The user interface may be configured for use by the user to enter, select or modify first responder or emergency contacts. The system may include a central or distributed network server 328. The user device 318, along with other user devices 330 and 332 such as may be used by other patients, may be configured to communicate with the server 328 through one or more networks 334. The server 328 may also be configured to communicate with electronic medical record systems to obtain clinical data 336 for the patients using the MNPEF or MNPMF therapy system. Digital communication through various wired and wireless network(s), including various combinations of Bluetooth, Wi-Fi, and cellular networks, may allow remote access to electronic medical records and may allow remote communication with clinics to enable remote clinical monitoring of data. The clinical data may be at the patient level 338 and may also be at patient population levels 340. Thus, the system may be capable optimizing or otherwise determining effective therapy by learning from patient-specific data and data from other patients. Clinical data for a control group may also be accessed. Other, non-clinical data 342 for the patients using the MNPEF or MNPMF therapy system (and potentially control group) may also be accessed. The server 328 may also be configured communicate with clinics to enable clinical monitoring 344. Thus, for example, remotely-located doctors may be informed when the therapy changes or when an emergency event occurs.

Each of the server(s) 328, the user device(s) 318, 330, 332, and the controller 310 may include at least one processor configured to implement instructions. A processor-based system may include one or more processors, such as one or more of the processors for the server(s) 328, the user device(s) 318, 330, 332, and the controller 310. The machine learning algorithms may be implemented using one or more processors. The machine learning algorithms may be implemented in one or more processors, or in one or more devices such as one or more of the server(s) 328, the user device(s) 318, 330, 332, and/or controllers 310. The processing may be performed using multiple devices, such that any one device may perform only part of the processes implemented for the machine learning process. The server(s) may retrieve all of the data inputs and perform the machine learning processes.

Figure 4:
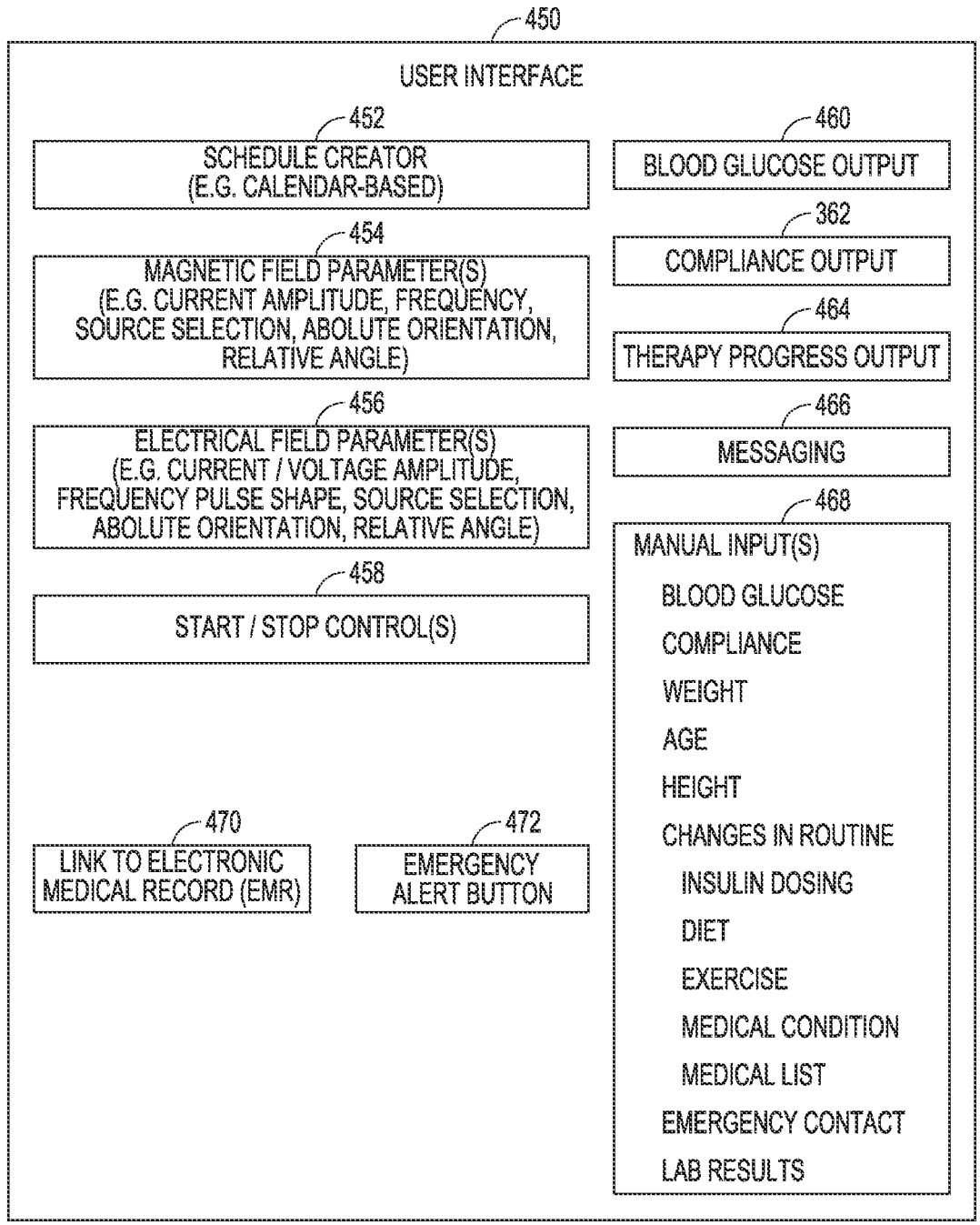
FIG. 4 illustrates, by way of example and not limitation, a user interface for a user device illustrated in FIG. 3.

FIG. 4 illustrates, by way of example and not limitation, an embodiment of a user interface for a user device illustrated FIG. 3. The illustrated user interface 450 includes a schedule creator 452 (such as a calendar-based scheduler), user interface elements to display, enter and modify magnetic field parameters 454 such a current amplitude, frequency, pulse shape, source selection, absolute orientation, relative angle and the like, and electric field parameters 456 such as current or voltage amplitude, frequency, pulse shape, source selection, absolute orientation, relative angle, and the like. The user interface also nay allow the user to manually start and/or stop the therapy 458.

The user interface may include outputs to present to the user blood glucose levels 460, compliance information 462, and therapy progress (e.g., 70% done or 2 hours left) 464. The user interface may include energy state information, indicating a current state of metabolic balance which includes the levels and stoichiotmetries of energy metabolites. The user interface may include redox state information. The user interface may include messaging capabilities 466 such as may be used to send and/or receive messages (e.g., video, voice and/or text) from clinicians, support staff, health coaches, first responders and emergency contacts. Examples of messaging may include various alerts, coaching comments, and questions regarding changes in diet, insulin intake, routine, condition (e.g., health, weight, and the like) or other medicine. For example, the machine learning algorithm may detect an unusual change in blood glucose levels that do not appear to have a good fit within the model absent some change in the patient's routine or condition. The model can then incorporate the requested information to further refine the model.

The user interface may be configured to receive manual inputs 468 (e.g., in response to prompts) to retrieve data that may be relevant to determining the efficacy of the MNPEF or MNPMF therapy that may be useful in optimizing the therapy. Examples of manual inputs may include, but are not limited to, one or more of blood glucose, compliance information, weight, age, height, emergency contacts, lab results, and changes in routine (e.g., change in insulin dosing, diet, exercise, medical condition, medicine list, and the like).

The user interface may be configured to obtain information to link the system to electronic medical records (EMR) of the patient 470. The user interface may include an emergency alert button or other element to contact first responders or emergency contacts when selected by the patient 472.

Figure 5:
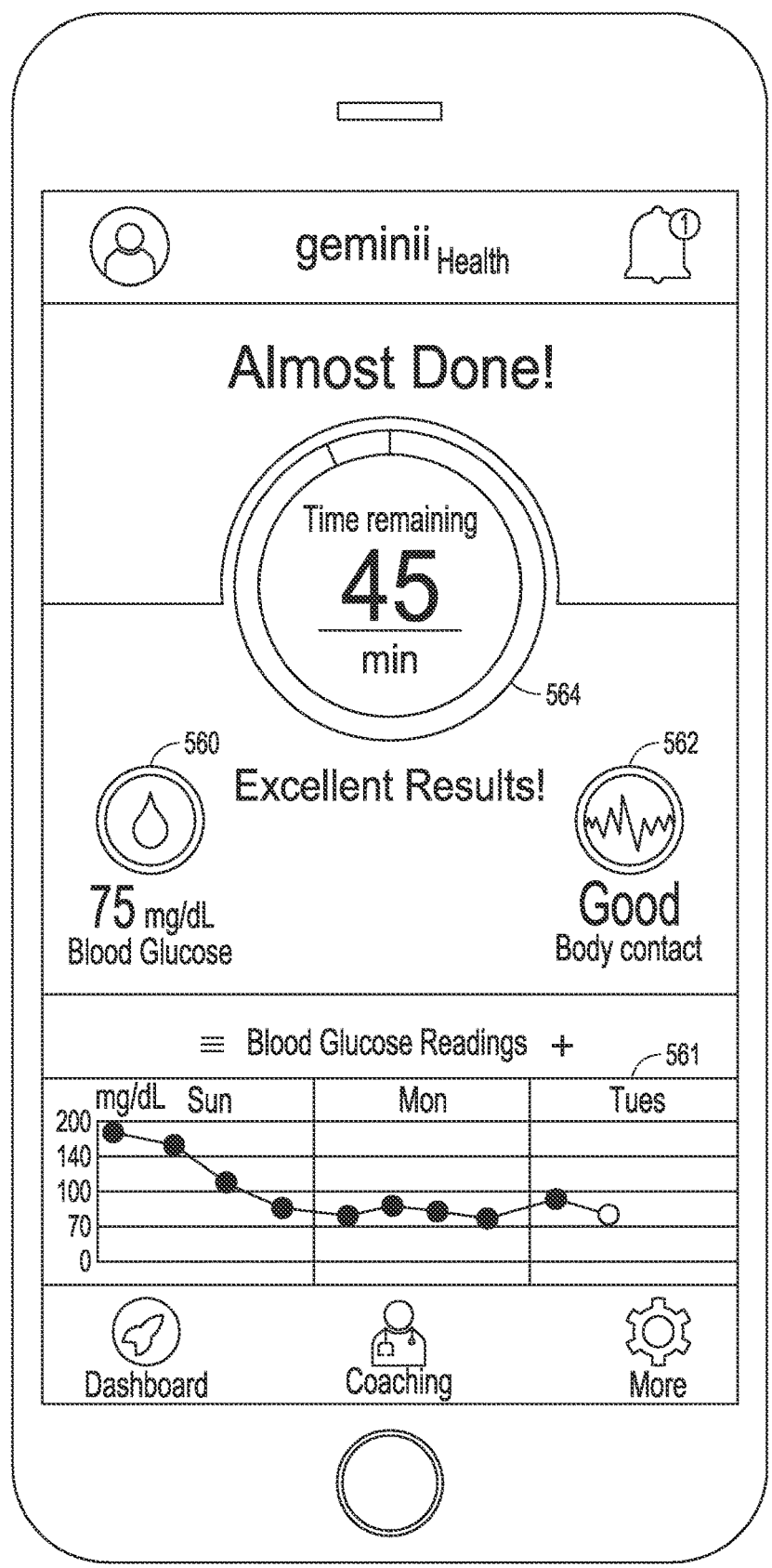
FIG. 5 illustrates, by way of example and not limitation, a user interface for a user device illustrated in FIG. 3.

FIG. 5 illustrates, by way of example and not limitation, a user interface for a user device illustrated in FIG. 3. Illustrated are specific examples of therapy progress 564, blood glucose output 560 along with a blood glucose trend 561, and a compliance output 562 illustrated as a body contact quality for a wearable device. In some embodiments, the app on the device may be configured to be friendly toward seeing-impaired patients. For example, the app may read the outputs of the user interface, may receive voice inputs, and may receive various sound or haptic signals as the user navigates the user interface. The app may but does not have to be incorporated in a smart phone.

Analytes/Biomarkers

By way of example and not limitation, the MNPEF or MNPMF therapies may be a therapeutic treatment for diabetes, cancer, obesity, inflammation, or glaucoma. Other chronic diseases and conditions may be treated. The metric(s) of the subject used by the machine learning algorithm to determine parameter(s) for the MNPEF or MNPMF therapies may include various analytes or biomarkers.

The term MOEF refers to "Magnetic Orthogonal Electric Field" and is a more specific embodiment of MNPEF, where the vector direction of the magnetic field is orthogonal or substantially orthogonal to the vector direction of the electric field within the targeted tissue. The biological effects of MOEFs are mediated by interaction with redox and metabolic systems. Carter C. S., H. S. C., Searby C. C., Cassaidy B., Miller M. J., Grzesik W. J., Piorczynski T. B., Zhang Q., Bradbery K., Pak T. K., Walsh S. A., Dick D. W., Akurathi V., Acevedo M., Mapuskar K. A., Milne G. L., Hinton A. O., Guo D. F., Falls-Hubert K. C., Wagner B. A., Carter W. A., Wang K., Norris A. W., Rahmouni K., Buettner G. R., Hansen J M., Spitz D. R., Abel E. D. and Sheffield V. C. Exposure to Static Magnetic and Electric Fields Treats Type 2 Diabetes. *Cell Metabolism* 32, 561-574 Oct. 6, 2020. Monitoring treatment efficacy is important to establish safe and effective dosing parameters. Fortunately, there are robust and chemically stable biomarkers within redox and metabolic systems that are useful as indicators of the biological and therapeutic efficacy of MOEFs. These include biomarkers of glucose metabolism, lipid peroxidation and oxidative stress which may be used individually or in combination to detect a positive therapeutic response of MOEFs: glucose, insulin, glucagon, HbA1c, glycogen, c-peptide, pyruvate, lactate, FGF21, GDF15, adiponectin, respiratory quotient (RQ) which is the volume of carbon dioxide produced divided by the amount of oxygen consumed, cortisol, F2-isoprostanes (e.g. 5-series, 12-series, 8-series and 15-series), a product of free radical mediated oxidation of arachidonic acid (see Sampson, M. J., Gopaul, N., Davies, T. R., Hughes, D. A. & Carrier, M. J. Plasma F2 Isoprostanes. *Diabetes Care* 25, 537 (2002); Milne, G. L., Sanchez, S. C., Musiek, E. S. & Morrow, J. D. Quantification of F2-isoprostanes as a biomarker of oxidative stress. *Nature protocols* 2, 221-226 (2007); Il, et al. Urinary F2-Isoprostanes as a Biomarker of Reduced Risk of Type 2 Diabetes. *Diabetes Care* 35, 173 (2012)), antioxidants such as the glutathione (GSH), glutathione disulfide (GSSG), cysteine (Cys), cystine (CysS), thioredoxin (Trx), peroxiredoxin (Prdx), glutathione-S-transferase (GST), glutathione peroxidase 3 (GPX3) which participate in neutralizing oxidants by supporting or directly donating reducing equivalents to reduce and neutralize oxidants (see Jones, D. P. Radical-free biology of oxidative stress. *Am J Physiol Cell Physiol* 295, C849-C868 (2008); Jones, D. P. & Sies, H. The Redox Code. *Antioxidants & redox signaling* 23, 734-746 (2015); Harris, L. S., et al. Glutathione and thioredoxin antioxidant pathways synergize to drive cancer initiation and progression. *Cancer cell* 27, 211-222 (2015); Hauffe, R., et alt GPx3 dysregulation impacts adipose tissue insulin receptor expression and sensitivity. *JCI Insight* 5(2020), expression of genes that induce the antioxidant response: NRF2, which translocates to the nucleus upon activation by oxidative stimuli where they induce expression of genes that mediate an antioxidant response (see Kansanen, E., Kuosmanen, S. M., Leinonen, H. & Levonen, A. L. The Keapl-Nrf2 pathway: Mechanisms of activation and dysregulation in cancer. *Redox Biol* 1, 45-49 (2013); Schmidlin, C. J., Dodson, M. B., Madhavan, L. & Zhang, D. D. Redox regulation by NRF2 in aging and disease. *Free Radical Biology and Medicine* 134, 702-707 (2019), expression of genes that are activated by NRF2 to mediate the antioxidant response: NAD(P)H dehydrogenase [quinone]1 (NQO1), heme oxygenase 1 (HMOX1), glutamate-cysteine ligase catalytic subunit (GCLC), glutamate-cysteine ligase regulatory subunit (GCLM) (see Kansanen et al.), the redox couples, $NADP\pm$, NADPH, NAD+, NADH, redox post-translational modifications such as glutathionylation, cysteinylation, nitrosylation, carbonylation etc.6, long-chain fatty acids (LCFAs) (e.g. myristate, myristoleate, pentadeconoate, palmitate, palmitoleate, margarate, 10-heptadecenoate, stearate, oleate, vaccinate, nonadecanoate, 10-nonadecenoate, arachidate, eicosenoate, erucate etc.), poly unsaturated fatty acids (PUFAs) (e.g. heneicosapentaenoate, tetradecadienoate, hexadecadienoate, hexadecatrienoate, stearidonate, eicosapentaenoate, docasapentaenoate, docosahexaenoate, docosatrienoate, nisinate, linoleate, linolenate, dihomo-linolenate, arachidonate, adrenate, docosapentaenoate, docosadienoate, dihomo-linoleate, mead acid, docosatrienoate), medium chain fatty acids (MCFAs) (e.g. heptanoate, cis-4-decenoate, 10-undecenoate, 5-dodecenoate etc.), fatty acids dicarboxylate (e.g. glutarate, 2-hydroxyglutarate, 2-hydroxyadipate, 3-hydroxyadipate, suberate, azelate, sebacate, dodecadienoate, dodecanedioate, tetradecanedioate, hexadecanedioate, octadecenedioate, tetradecadienedioate, 3-carbodyy-4-methyl-5-propyl-2-furanpropanoate, 3-carboxy-4-methyl-5-pentyl-2-furanpropionate etc.), amino fatty acids (e.g. 2-aminoheptanoate, 2-aminooctanoate, n-acetyl-2-aminooctanoate etc.), acyl glycine (e.g. isocaproylglycine, valerylglycine, hexanoylglycine, 4-methyihexanoyigiycine, trans-2-hexanoylglycine, n-octanoylglycine, 2-butanoylglycine, 3-hydroxybutyroylglycine etc.) and carnitines (e.g. acetylcarnitine, (1R)-3-hydroxybutyrylcarnitine, hexanoylcarnitine, octanoylcarnitine, decanoylcarnitine, 5-dodecenoylcarnitine, cis-4-decenoylcarnitine, laurylcarnitine, myristoylcarnitine, palmitoylcarnitine palmitoleoylcarnitine, stearoylcarnitine, linoleoylcarnitine, linolenoylcarnitine, 3-hydroxyoleoylcarnitine, oleoylcarnitine, myristoleoylcarnitine, adipoylcarnitine, octadecenedioylcarnitine, arachidoylcarnitine, arachidonoylcarnitine, behenoylcarnitine, dihorno-linolenoylcarnitine, dihomo-linolcoylcarnitine, eicosenoylcarnitine, docosahexaenoylcarnitine, lignoceroylcarnitine, nervonoylcarnitine, margaroylcarnitine, pentadecanoylcarnitine, 3-hydroxypahmitoyicarnitine, deoxycarnitine, carnitine etc.) and beta-hydroxybutyrate. The redox potential is a robust biomarker to assess the safety and efficacy of MOEF. The redox potential is calculated by the Nernst equation ($E_o - RT/nF$ In [reduced]2/[oxidized]) to yield a half-cell reduction potential ($E_h$) for the couple, where $E_o$ is the standard half-cell reduction potential for the redox couple, R is the gas constant, T is the absolute temperature, n is 2 for the number of electrons transferred, and F is Faraday's constant. Schafer, F. Q. & Buettner, G. R. Redox environment of the cell as viewed through the redox state of the glutathione disulfide/glutathione couple. *Free Radical Biology and Medicine* 30, 1191-1212 (2001).

Metabolism, including both catabolic and anabolic pathways, is an optimally synchronized set of oxidation and reduction reactions (redox). Metabolism both produces ROS/RNS and is regulated by direct changes in the levels of ROS/RNS or indirectly, by activation of protein signaling via ROS/RNS or other induced secondary messengers. The regulation of ROS/RNS production is tightly controlled via a pro-oxidant-antioxidant system. Likewise, the inflammatory response used by immune cells leverages the same metabolic pathways to produce ROS/RNS to defend against pathogens and exogenous toxins and resets to basal levels via redox regulation through the tightly controlled pro-oxidant-antioxidant system. Aberrations in redox regulation and the nutrients supplied to immune cells can lead to disease states due to chronic systemic inflammation. Therefore, since MOEFs modulate redox, MOF's may also be effective in treating inflammatory disease including infectious disease.

As a result of metabolism and the regulation of redox, these biomarkers can be detected in a variety of tissues, extracellular spaces and bodily fluids including but not limited to whole blood, plasma, serum, red blood cells, tears, urine, stool, cerebrospinal fluid, lymphatic fluid etc. These biomarkers are to be measured in subjects receiving treatment and compared to control samples which can be classified as the same subject before receiving treatment (paired sample) or an independent group of subjects that are matched to the subject receiving treatment in age, sex, disease type (e.g. type 2 diabetes, cancer, obesity, chronic kidney disease, Alzheimer's disease, depression, opioid addiction) that have not received treatment (independent sample) or a historical control (independent but retrospective sample). The above biomarkers of MOEF may be used to determine treatment efficacy and safety in a wide range of metabolic and redox-related diseases and conditions such as type 2 diabetes, type 1 diabetes, cancer (e.g. liver, cancer, pancreatic cancer, bladder cancer, stomach cancer, colon cancer, breast cancer, prostate cancer, lung cancer, brain cancer, melanoma, lymphoma, sarcoma or leukemia), obesity, steatosis, glaucoma, retinopathy, aging, Alzheimer's disease, Parkinson's disease, Multiple Sclerosis, depression, Schizophrenia, addiction (e.g. alcoholism, opiate addiction etc.), inflammatory disease (e.g. gout, hepatitis (viral and NAFLD induced), Crohn's disease, celiac disease, ulcerative colitis, glomerulonephritis, lupus, rheumatoid arthritis, osteoarthritis, ankylosing spondylitis, myositis, amyloidosis, asthma, chronic obstructive pulmonary disease, atopic dermatitis, psoriasis, atherosclerosis, reperfusion injury, transplant rejection, and autoimmune diseases), and infectious disease.

Treatment with MNPEF reduces fasting blood glucose (FBG) in two different models of type 2 diabetes (T2D), does not increase levels of insulin which is consistent with an insulin-sensitizing effect, reduces HOMA-IR a measurement of insulin resistance, and reduces HbA1c in both type I diabetes (T1D) and type 2 diabetes (T2D). Positive treatment effect in normal healthy and diabetic animal models is correlated with significant reductions in circulating levels of F2-isoprostanes. Significant increases in GSH in plasma and liver are observed in diabetic animal models upon treatment with MOEFs. Significant reductions in glutathionylation and cysteinylation occur with MOEF treatment for 3 days in diabetic animal models (protein S-glutathionylation (PrSSG) and protein S-cysteinylation (PrCysS)) (see Dalle-Donne, L., Rossi, R., Colombo, G., Giustarini, D. and Milzani, A., Protein S-glutathionylation: a regulatory device from bacteria to humans. *Trends in Biochemical Sciences* 34, 86-96 (2008). MOEF treatment for 3 days produced a redox environment that was significantly more reducing than in untreated diabetic animals. Significant elevations in NRF2 nuclear localization was found after 3 days of MOEF treatment in diabetic animal models. When oxidative stress is reduced, levels of F2-isoprostanes are expected whereas increases in oxidative stress is associated with increases in F2-isoprostanes. Similarly, elevated levels of GSH are associated with lower oxidative stress.

Significant reductions in circulating (plasma) fatty acids including, MCFA, LCFA, PUFA, fatty acid dicarboxylates, acyl glycines, amino fatty acids, and significant increases in carnitines occur with 3 days of MOEF treatment in diabetic animal models.

Based on these data, one or more of the biomarkers listed above or various combinations of two or more of the biomarkers listed above may be used to determine safety and efficacy in various disease states listed above.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising
    a processor-based system including at least one processor; and
    memory including instructions, which when executed by the processor-based system, cause the processor-based system to:
        access metrics of a subject who is being treated with a therapy that includes a magnetic non-parallel electric field (MNPEF) therapy or a magnetic non-parallel magnetic field (MNPMF) therapy, wherein the accessed metrics include:
            data for at least one analyte, the data for the at least one analyte including one or more of blood glucose data, lactate data, pyruvate data, free fatty acid data, cholesterol data; and
            compliance data for complying with the therapy;
        use the accessed metrics as an input to a machine learning algorithm that is configured to determine a set of therapy parameters for the therapy based on the accessed metrics, the machine learning algorithm being configured to continually improve a model for determining the set of therapy parameters based on the accessed metrics; and
        program a controller operably connected to at least one energy field system to deliver the therapy according to the determined set of therapy parameters.

2. The system of claim 1, further comprising a continuous glucose monitor (CGM) configured to provide the blood glucose data.

3. The system of claim 1, wherein the accessed metrics used as the input to the machine learning algorithm include A1c (HbA1c) data and/or energy metabolite data.

4. The system of claim 1, wherein the accessed metrics used as the input to the machine learning algorithm include redox status data.

5. The system of claim 1, wherein the accessed metrics used as the input to the machine learning algorithm include at least one of: genetics, weight, height, body mass index (BMI), blood gases, ethnicity, sex, fat mass, muscle mass, age, comorbidities, concurrent medications, sleep quality, brainwaves, heart rate or blood pressure.

6. The system of claim 1, wherein the accessed metrics include data from at least one sensor or data from at least one remotely-accessed medical record.

7. The system of claim 1, wherein the accessed metrics include questionnaires, diaries, clinician reports, or rating scales.

8. The system of claim 1, wherein the machine learning algorithm includes a genetic algorithm, a neural network, a reinforcement learning strategy, a gradient descent process, Bayesian, clustering, decision tree, linear regression or rule-based algorithms.

9. The system of claim 1, wherein the machine learning algorithm is configured to determine a schedule or a duration of the therapy.

10. The system of claim 1, wherein the machine learning algorithm is configured to determine an amplitude, frequency or duration of an energy signal used to deliver the therapy.

11. The system of claim 1, further comprising a user interface configured to output a blood glucose level, energy state information, redox state information, compliance information, and therapy progress.

12. The system of claim 11, wherein the user interface is configured to use an audio, visual or tactile signal when outputting the blood glucose level, the energy state information, the redox state information, the compliance information and the therapy progress.

13. The system of claim 11, wherein the user interface is configured for use in remotely messaging clinicians, support staff, health coaches, first responders or emergency contacts.

14. The system of claim 1, wherein the processor-based system is configured to coordinate the therapy with insulin doses provided by an insulin pump, with chemotherapies, with radiation therapies, with immunotherapies, with antimicrobial therapies, with anti-inflammatory therapies, or with tissue transplantation.

15. The system of claim 1, wherein the input to the machine learning algorithm includes both patient-specific data and data from other patients.

16. A method comprising using a processor-based system that includes at least one processor to:
- access metrics of a subject who is being treated with a therapy that includes a magnetic non-parallel electric field (MNPEF) or magnetic non-parallel magnetic field (MNPMF) therapy, wherein the accessed metrics include:
  - data for at least one analyte, the data for the at least one analyte including one or more of blood glucose data, lactate data, pyruvate data, free fatty acid data, or cholesterol data; and
  - compliance data for complying with the therapy;
- use the accessed metrics as an input to a machine learning algorithm that is configured to determine a set of therapy parameters for the therapy based on the accessed metrics, the machine learning algorithm being configured to continually improve a model for determining the set of therapy parameters based on the accessed metrics; and
- program a controller operably connected to at least one energy field system to deliver the therapy according to the determined set of therapy parameters.

17. The method of claim 16, wherein the accessed metrics include a trend of the blood glucose data obtained by a continuous glucose monitor (CGM).

18. The method of claim 16, wherein the accessed metrics include at least one of Ale (HbA1c) data, energy metabolite data, or redox status data.

19. The method of claim 16, further comprising using digital communication to report changes in therapy or patient metrics to remotely-located clinicians or technicians.

20. The method of claim 16, further comprising using audio, visual or tactile signals to output a blood glucose level, energy state information, redox state information, a compliance information and a therapy progress.

21. A method for treating a condition using a therapy that includes a magnetic non-parallel electric field (MNPEF) or magnetic non-parallel magnetic field (MNPMF) therapy, the method comprising using a processor-based system that includes at least one processor to:
- access data for at least one analyte of a subject who is being treated with the therapy;
- use the data for the at least one analyte as an input to a machine learning algorithm that is configured to determine a set of therapy parameters for the therapy based on the data for the at least one analyte, the machine learning algorithm being configured to continually improve a model for determining the set of therapy parameters based on the data for the at least one analyte; and
- program a controller operably connected to at least one energy field system to deliver the therapy using the determined set of therapy parameters.

22. The method of claim 21, wherein the condition treated using the therapy includes diabetes, cancer, obesity, inflammation, neurodegeneration or glaucoma.

* * * * *